US010039897B2

(12) United States Patent
Norris et al.

(10) Patent No.: US 10,039,897 B2
(45) Date of Patent: Aug. 7, 2018

(54) RETENTION APPARATUS

(71) Applicant: Nuvectra Corporation, Plano, TX (US)

(72) Inventors: Carole L. Norris, Saint Paul, MN (US); Elliot Bridgeman, Big Lake, MN (US)

(73) Assignee: Nuvectra Corporation, Plano, TX (US)

(*) Notice: Subject to any disclaimer, the term of this patent is extended or adjusted under 35 U.S.C. 154(b) by 226 days.

(21) Appl. No.: 14/595,583

(22) Filed: Jan. 13, 2015

(65) Prior Publication Data

US 2015/0196379 A1 Jul. 16, 2015

Related U.S. Application Data

(60) Provisional application No. 61/926,610, filed on Jan. 13, 2014.

(51) Int. Cl.

| | |
|---|---|
| ***B65D 6/04*** | (2006.01) |
| ***A61M 25/00*** | (2006.01) |
| ***A61B 50/20*** | (2016.01) |
| ***A61B 50/33*** | (2016.01) |

(52) U.S. Cl.

CPC .......... *A61M 25/002* (2013.01); *A61B 50/20* (2016.02); *A61B 50/33* (2016.02)

(58) Field of Classification Search

CPC .... A61F 2/0095; A61M 25/002; A61B 50/33; A61B 50/20; A47G 19/04; A47G 23/0225; A47G 23/0633; A47G 23/06; Y10T 24/4465; Y10T 24/44274; Y10T 24/44778; Y10T 403/7007; F16B 2/20; F16B 2/22; B60P 7/0815; B60R 5/04

USPC ....... 22/20 R, 20 CW, 22, 23 R; 206/231.81; 248/231.81, 229.16, 229.26, 228.7, 230.7, 248/689, 690, 316.1, 316.7, 309.1; 403/DIG. 7, 349; 606/75, 151, 157, 606/914–916, 232

See application file for complete search history.

(56) References Cited

U.S. PATENT DOCUMENTS

| | | | | | |
|---|---|---|---|---|---|
| 1,379,476 | A * | 5/1921 | Parr | B65D 45/32 | 24/20 CW |
| 3,128,514 | A * | 4/1964 | Parker | A44B 18/00 | 2/300 |
| 4,887,324 | A * | 12/1989 | Cairns | A47K 3/38 | 160/327 |
| 5,056,658 | A * | 10/1991 | Sobel | A61B 17/06133 | 206/380 |
| 5,131,533 | A * | 7/1992 | Alpern | A61B 17/06133 | 206/380 |
| 5,503,266 | A * | 4/1996 | Kalbfeld | A61B 17/06133 | 206/380 |
| 6,165,204 | A * | 12/2000 | Levinson | A61B 17/0487 | 606/151 |
| 8,272,508 | B2 * | 9/2012 | Bettenhausen | A61L 2/26 | 206/370 |
| 8,893,883 | B2 * | 11/2014 | Valaie | A61L 2/26 | 206/363 |

(Continued)

*Primary Examiner* — Anthony Stashick
*Assistant Examiner* — James M Van Buskirk
(74) *Attorney, Agent, or Firm* — Haynes and Boone, LLP

(57) ABSTRACT

In various examples, an apparatus includes a tray including a channel configured to hold a therapy delivery element at least partially within the channel. A retention clip is sized and shaped to fit within a portion of the channel. The retention clip is configured to releasably retain the therapy delivery element within the retention clip.

20 Claims, 4 Drawing Sheets

(56) References Cited

U.S. PATENT DOCUMENTS

| | | | | |
|---|---|---|---|---|
| 2003/0006151 | A1* | 1/2003 | Lin | A47G 19/02 206/216 |
| 2012/0189382 | A1* | 7/2012 | Health | B60P 7/0815 403/349 |

* cited by examiner

RETENTION APPARATUS

CROSS REFERENCE TO RELATED APPLICATIONS

This application claims the benefit of priority to U.S. Provisional Application Ser. No. 61/926,610, filed on Jan. 13, 2014, entitled "RETENTION APPARATUS," which is incorporated by reference herein in its entirety.

TECHNICAL FIELD

The present invention relates to a retention apparatus, and more specifically relates to a retention clip configured to maintain a therapy delivery element within a packaging tray.

BACKGROUND

Medical device packaging, in some instances, is used to provide containment of therapy delivery devices or other products during distribution and handling. In some instances, medical devices use rigid, formed packaging (for instance, trays) to preserve sterility and provide protection of potentially fragile and/or expensive medical device products. During package opening, a medical device can migrate free from the packaging and incur damage or loss of sterility.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the subject matter can be used to retain a therapy delivery element (for instance, a stimulation lead) within packaging, thereby decreasing the chances of the therapy delivery element from inadvertently coming out of the packaging and potentially becoming damaged and/or losing sterility. To better illustrate the apparatuses, systems, and methods described herein, a non-limiting list of examples is provided here:

Example 1 can include subject matter that can include a retention apparatus including a tray including a channel configured to hold a therapy delivery element at least partially within the channel. A retention clip is sized and shaped to fit within a portion of the channel, the retention clip being configured to releasably retain the therapy delivery element within the retention clip.

In Example 2, the subject matter of Example 1 is optionally configured such that the retention clip includes a first end and a second end. With the retention clip disposed within the portion of the channel, the first end is disposed proximate the second end such that the retention clip forms a substantially closed loop to releasably retain the therapy delivery element.

In Example 3, the subject matter of Example 2 is optionally configured such that, with the retention clip disposed within the portion of the channel, the first end and the second end overlap.

In Example 4, the subject matter of any one of Examples 2-3 is optionally configured such that the retention clip includes a substantially triangular shape with a first side of the retention clip including the first end and a second side of the retention clip including the second end.

In Example 5, the subject matter of Example 4 is optionally configured such that the first side and the second side of the retention clip are each attached to a third side of the retention clip.

In Example 6, the subject matter of Example 5 is optionally configured such that a first hinge is disposed between the first side and the third side.

In Example 7, the subject matter of Example 6 is optionally configured such that the first hinge includes a living hinge.

In Example 8, the subject matter of any one of Examples 6-7 is optionally configured such that a second hinge is disposed between the second side and the third side.

In Example 9, the subject matter of Example 8 is optionally configured such that at least one of the first hinge and the second hinge includes a living hinge.

In Example 10, the subject matter of any one of Examples 1-9 is optionally configured such that the portion of the channel includes a recess, a shape of the recess being complementary to a shape of the retention clip.

Example 11, the subject matter of any one of Examples 1-10 is optionally configured such that the retention clip includes a silicone material.

In Example 12, the subject matter of any one of Examples 1-11 is optionally configured such that the tray includes a polyethylene terephthalate glycol-modified (PETG) material.

Example 13, the subject matter of any one of Examples 1-12 is optionally configured such that the retention clip is configured to stick to the tray.

In Example 14, the subject matter of any one of Examples 1-13 is optionally configured such that the portion of the channel includes a lip configured to inhibit removal of the retention clip from the tray.

Example 15 can include, or can optionally be combined with any one of Examples 1-14 to include subject matter that can include a retention clip including a first end and a second end. The first end is biased proximate the second end such that the retention clip forms a substantially closed loop, wherein the retention clip is configured to releasably retain a therapy delivery element within the retention clip.

In Example 16, the subject matter of Example 15 is optionally configured such that the retention clip is sized and shaped to fit within a complementary portion of a channel of a tray.

In Example 17, the subject matter of any one of Examples 15-16 is optionally configured such that the first end and the second end overlap.

In Example 18, the subject matter of any one of Examples 15-17 is optionally configured such that the retention clip includes a substantially triangular shape with a first side of the retention clip including the first end and a second side of the retention clip including the second end.

In Example 19, the subject matter of Example 18 is optionally configured such that the first side and the second side of the retention clip are each attached to a third side of the retention clip.

In Example 20, the subject matter of Example 19 optionally includes a hinge disposed between at least one of: the first side and the third side; and the second side and the third side.

DETAILED DESCRIPTION

The present patent application relates to a retention apparatus for providing retention of a product, such as a medical device product, within packaging. For instance, the apparatus of the present patent application is used, in some examples, to retain a therapy delivery element, such as a stimulation lead, for instance, within packaging until which point a physician or other caregiver removes the therapy delivery element from the apparatus and the packaging.

Figure 1:
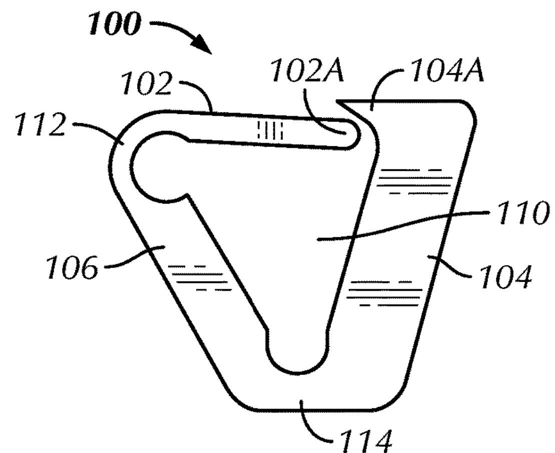
FIG. 1 is an end view of a retention clip in accordance with at least one example of the invention.
Figure 2:
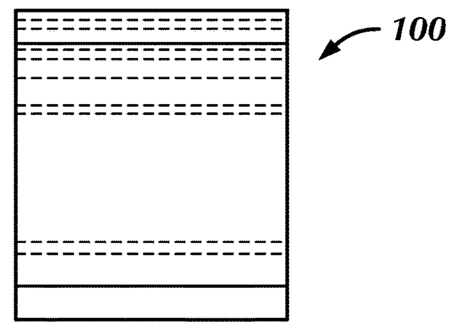
FIG. 2 is a side view of a retention clip in accordance with at least one example of the invention.
Figure 3:
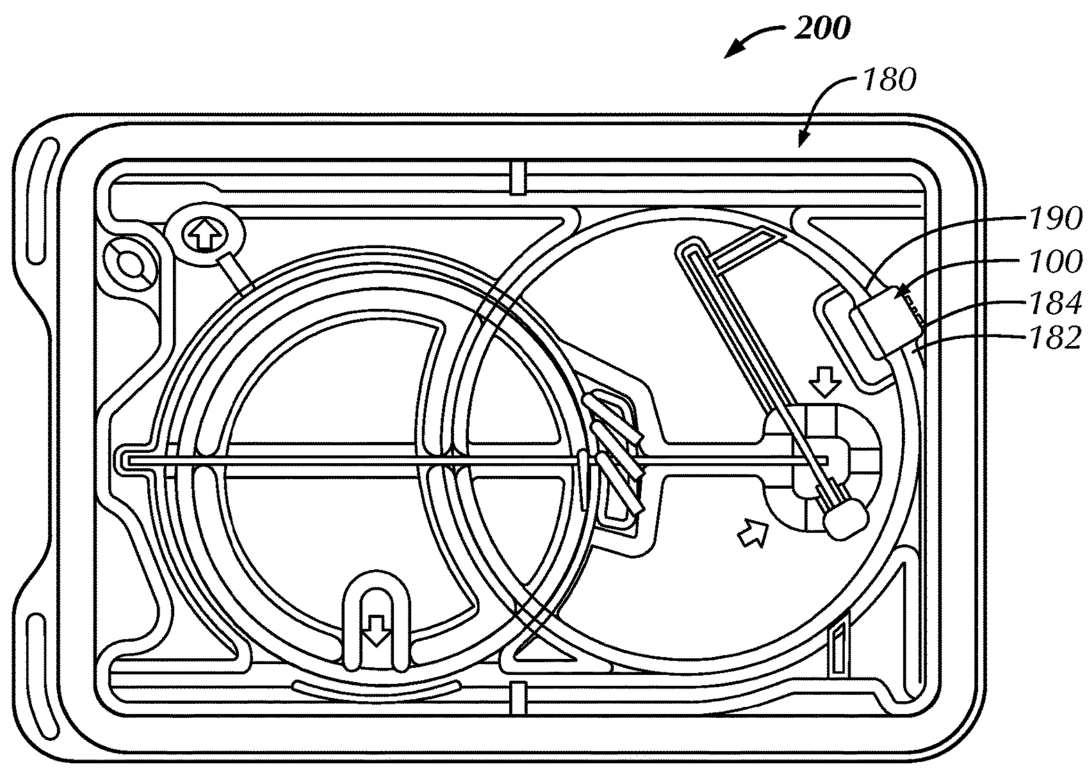
FIG. 3 is a top view of a tray and a retention clip in accordance with at least one example of the invention.

Referring to FIGS. 1-3, a retention apparatus 200, in various examples, includes a tray 180 including a channel 182 configured to hold a therapy delivery element 190 at least partially within the channel 182. The therapy delivery element 190, in various examples, can include a pacing lead, a defibrillation lead, a stimulation lead, a sensing lead, a fluid delivery conduit, or any combination thereof. In some examples, a retention clip 100 is sized and shaped to fit within a portion 184 of the channel 182. In some examples, the retention clip 100 is configured to releasably retain the therapy delivery element 190 within the retention clip 100.

In some examples, the retention clip includes a first end 102A and a second end 104A. In further examples, with the retention clip 100 disposed within the portion 184 of the channel 182, the first end 102A is disposed proximate the second end 104A such that the retention clip 100 forms a substantially closed loop to releasably retain the therapy delivery element 190. That is, with the first end 102A and the second end 104A disposed proximate to each other, an object, such as the therapy delivery element 190, for instance, placed within an interior 110 of the retention clip 100 can be retained within the interior 110 by the substantially closed loop formed by the retention clip 100. If it is desired to remove the therapy delivery element 190 from within the interior 110 of the retention clip 100, a physician or other user can pull on the therapy delivery element 190 with a force sufficient to spread the first end 102A from the second end 104A a sufficient distance to allow the therapy delivery element 190 to pass between the first and second ends 102A, 104A and exit the interior 110 of the retention clip 100. However, the therapy delivery element 190 can otherwise be retained by the retention apparatus 200 at other times (prior to the time when it is desired to remove the therapy delivery element 190 from the retention apparatus 200), such as during the acts of opening the retention apparatus 200 holding the therapy delivery element 190, moving the retention apparatus 200 holding the therapy delivery element 190, or otherwise handling the retention apparatus 200 when it is not intended for the therapy delivery element 190 to be removed from the retention apparatus 200. In this way, the retention clip 100 and the tray 180 of the retention apparatus 200, in some examples, can inhibit the therapy delivery element 190 from migrating free from the packaging inadvertently and incurring damage, loss of sterility, or the like.

In some examples, with the retention clip 100 disposed within the portion 184 of the channel 182, the first end 102A and the second end 104A overlap. That is, in some examples, at least a portion of the first end 102A overlaps at least a portion of the second end 104A or vice versa to fbrm the substantially closed loop of the retention clip 100. In some examples, the first end 102A of the retention clip 100 is biased proximate the second end 104A such that the retention clip 100 forms the substantially closed loop configured to releasably retain the therapy delivery element 190 within the retention clip 100.

In some examples, the retention clip 100 includes a substantially triangular shape with a first side 102 of the retention clip 100 including the first end 102A and a second side 104 of the retention clip 100 including the second end 104A. In various examples, the retention clip can include other shapes, including, but not limited to, a rectangular shape, a circular shape, an ovular shape, a polygonal shape, or a rounded shape, for instance.

In some examples, the first side 102 and the second side 104 of the retention clip 100 are each attached to a third side 106 of the retention clip 100. In this way, the retention clip 100, in some examples, forms a substantially triangular shape. The first side 102, in some examples, is configured to move with respect to the third side 106. For instance, the first side 102 is configured to be movable with respect to the third side 106 to allow separation of the first end 102A from the second end 104A to allow the therapy delivery element 190 to be selectively removed from within the retention clip 100. In some examples, a material of the retention clip 100 disposed between the first side 102 and the third side 106 is thinned to facilitate flexing between the first side 102 and the third side 106. In some examples, the retention clip 100 includes a first hinge 112 disposed between the first side 102 and the third side 106. In some examples, the first hinge 112 includes a living hinge. In other examples, the first hinge 112 can include other hinge configurations or mechanisms provided the hinge configuration or mechanism allows movement of the first side of the retention clip with respect to the third side of the retention clip. In still other examples, the retention clip can rely on one or more material properties of the retention clip (in addition to or instead of the first hinge) to allow movement of the first side with respect to the third side. For instance, the retention clip 100, in some examples, can be at least partially formed from a flexible material that allows bending of a portion of the retention clip 100 to allow movement of the first end 102A relative to the second end 104A and/or the first side 102 with respect to the third side 106.

The second side 104, in some examples, is configured to move with respect to the third side 106 in addition to or instead of the first side 102 being configured to move with respect to the third side 106. For instance, the second side 104 can be configured to be movable with respect to the third side 106 to allow separation of the first end 102A from the second end 104A to allow the therapy delivery element 190 to be selectively removed from within the retention clip 100.

Figure 6:
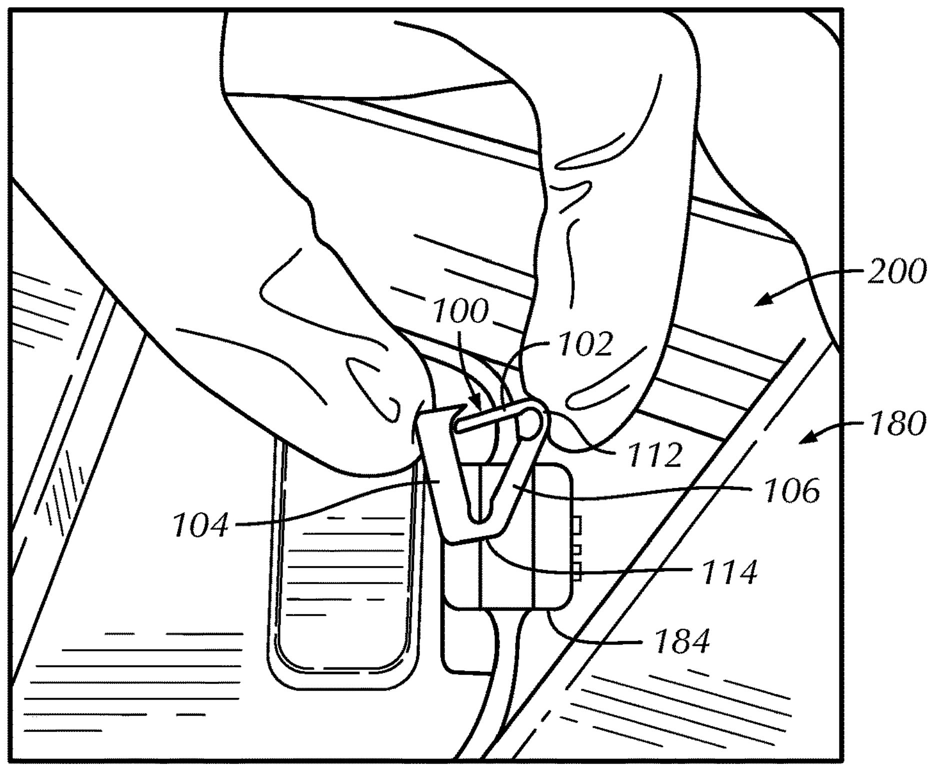
FIG. 6 is a perspective view of a retention clip being attached to a tray in accordance with at least one example of the invention.

In some examples, the second side 104 can be configured to be movable with respect to the third side 106 to allow the retention clip 100 to be compressed to fit within the portion 184 of the tray 180 (see FIG. 6). In some examples, a material of the retention clip 100 disposed between the second side 104 and the third side 106 is thinned to facilitate flexing between the second side 104 and the third side 106. In some examples, the retention clip 100 includes a second hinge 114 disposed between the second side 104 and the third side 106. In some examples, the second hinge 114 includes a living hinge in addition to or instead of the living hinge of the first hinge 112. In other examples, the second hinge 114 can include other hinge configurations or mechanisms provided the hinge configuration or mechanism allows movement of the second side of the retention clip with respect to the third side of the retention clip. In still other examples, the retention clip 100 can rely on one or more material properties of the retention clip 100 (in addition to or instead of the second hinge 114) to allow movement of the second side 104 with respect to the third side 106. For instance, the retention clip 100, in some examples, can be at least partially formed from a flexible material that allows bending of a portion of the retention clip 100 to allow movement of the first end 102A relative to the second end 104A and/or the second side 104 with respect to the third side 106.

Figure 4:
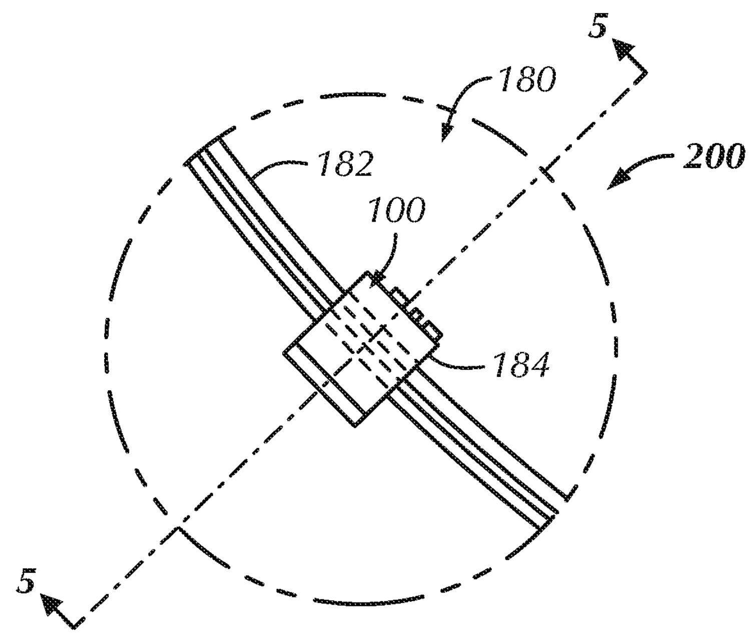
FIG. 4 is an enlarged top view of a retention clip engaged with a tray in accordance with at least one example of the invention.
Figure 5:
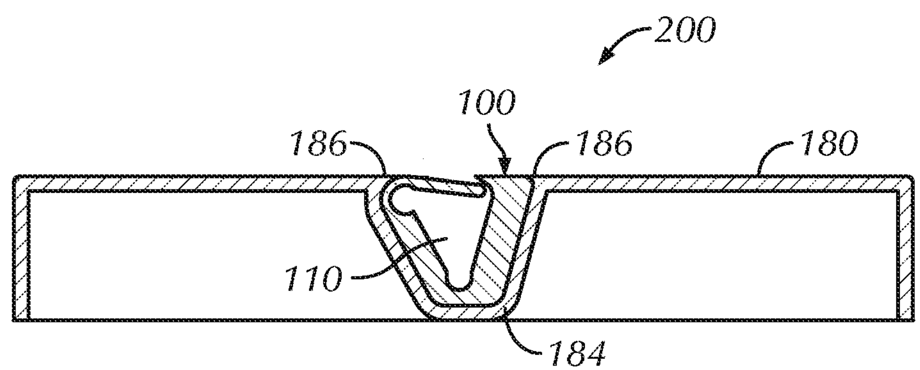
FIG. 5 is a cross-sectional view of the retention clip of FIG. 4, the cross section taken along line 5-5.

Referring to FIGS. 4 and 5, in some examples, the portion 184 of the channel 182 includes a recess 184. In some examples, a shape of the recess 184 is complementary to a shape of the retention clip 100. For instance, in examples with the shape of the retention clip 100 being substantially triangular, the recess 184 can include a complementary, substantially triangular shape in cross section (FIG. 5). In other examples in which the retention clip includes a shape other than substantially triangular, the shape of the recess can be complementary to that shape to allow the retention clip to fit snugly within the recess. In some examples, the portion or recess 184 of the channel 182 is undercut to form a lip 186 configured to inhibit removal of the retention clip 100 from the tray 180. In some examples, the lip 186 is formed proximate a top of the recess 184. In some examples, the lip 186 is formed along at least one side of the recess 184. In some examples, the lip 186 is formed along at least two sides of the recess 184. In further examples, the lip 186 is formed along at least two opposing sides of the recess 184. In some examples, the at least one lip 186 extends partially over the retention clip 100 with the retention clip 100 disposed within the recess 184, the at least one lip 186 at least partially constraining the retention clip 100 to inhibit the retention clip 100 from slipping out of the recess 184, for instance, if the therapy deliver element 190 is pulled to pass the therapy delivery element 190 between the first and second ends 102A, 104A to remove the therapy delivery element 190 from within the interior 110 of the retention clip 100.

In some examples, the retention clip 100 is configured to stick to the tray 180. For instance, in some examples, the retention clip 100 and the tray 180 are at least partially formed from materials that have a relatively high coefficient of friction between the materials. In some examples, the retention clip 100 includes a silicone material. In some examples, the tray 120 includes a polyethylene terephthalate glycol-modified (PETG) material. In some examples, the silicone material of the retention clip 100 grips the PETG material of the tray 180 and inhibits slippage of the retention clip 100 from within the recess 184 of the tray 180. In some examples, the grip of the material of the retention clip 100 to the material of the tray 180 is used in conjunction with the at least one lip 186 of the recess 184 to inhibit removal of the retention clip 100 from within the recess 184 of the tray 180, for instance during removal of the therapy delivery element 190 from within the interior 110 of the retention clip 100. In other examples, the grip of the material of the retention clip 100 to the material of the tray 180 is solely used to inhibit removal of the retention clip 100 from within the recess 184.

Figure 7:
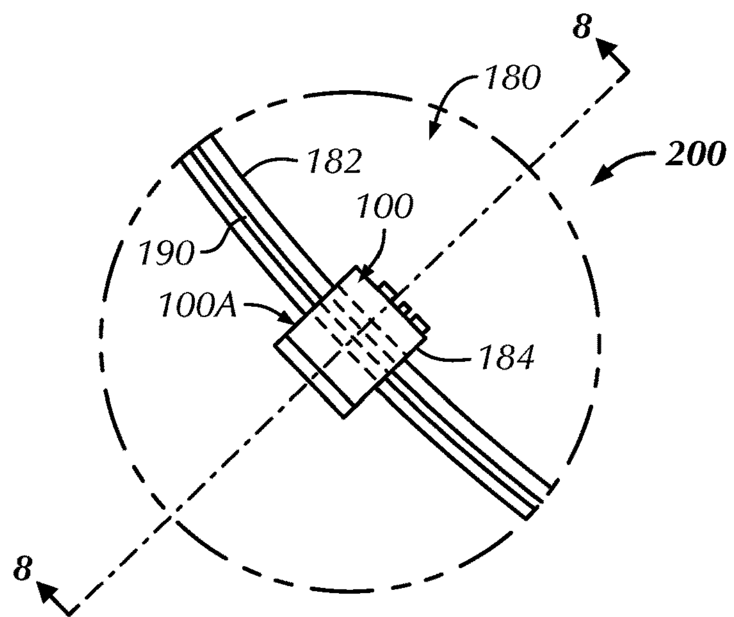
FIG. 7 is an enlarged top view of a retention clip engaged with a tray in accordance with at least one example of the invention.
Figure 8A:
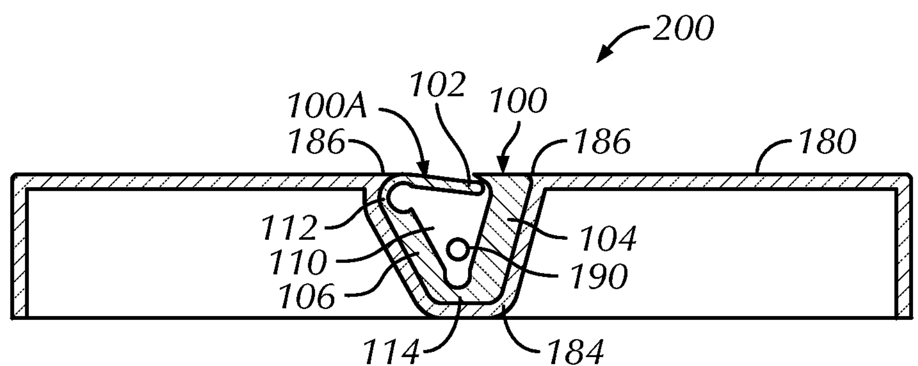
FIG. 8A is a cross-sectional view of the retention clip of FIG. 7 with a therapy delivery element retained within the retention clip, the cross section taken along line 8-8.
Figure 8B:
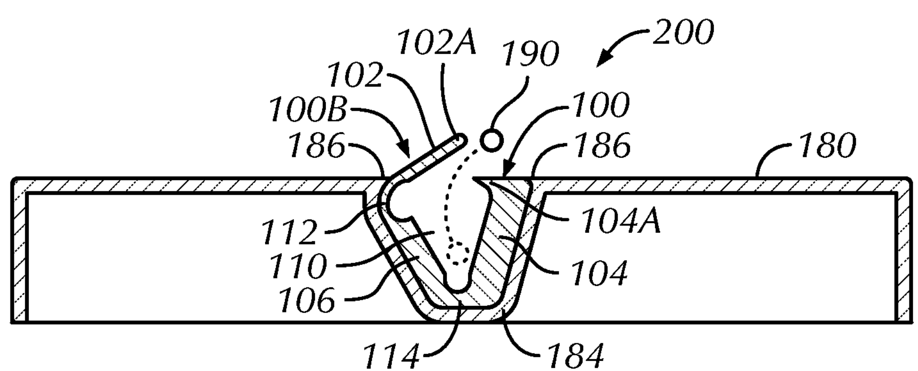
FIG. 8B is a cross-sectional view of the retention clip of FIG. 7 with a therapy delivery element removed from within the retention clip, the cross section taken along line 8-8.

Referring to FIGS. 6-8B, in some examples, in use, the retention clip 100 can be placed within the recess 184 of the tray 180. In some examples, the second and third sides 104, 106 of the retention clip 100 can be compressed toward one another, as shown in FIG. 6, by a packaging assembler in order to fit the retention clip 100 within the recess 186. The therapy delivery element 190, in various examples, can be placed within the retention clip 100 before or after the retention clip 100 is disposed within the recess 184 of the tray 180. With the retention clip 100 disposed within the recess 184 and a portion of the therapy delivery element 190 disposed within the interior 110 of the retention clip 100 with the retention clip 100 in a closed configuration 100A, as shown in FIGS. 7 and 8A, the retention apparatus 200 can be sealed or otherwise prepared for transport, handling, storage, or the like. In some examples, a remainder of the therapy delivery element 190 can be placed within the channel 182 of the tray 180 or otherwise disposed within the tray 180. When it is desired to remove the therapy delivery element 190 from within the retention apparatus 200, in some examples, the tray 180 can be opened or otherwise unsealed. In some examples, with the therapy delivery element 190 disposed within the retention apparatus 200, the retention clip 100 constrains the therapy delivery element 190 from inadvertently coming out of the retention apparatus 200 and potentially becoming damaged and/or losing sterility, for instance, when the retention apparatus 200 has been unsealed or otherwise opened. When it is desired to remove the therapy delivery element 190 from within the retention apparatus 200, the physician or other user can grasp the therapy delivery element 190 and pull it outwardly from the retention clip 100 to pull the first side 102 outwardly and separate the first end 102A from the second end 104A a distance sufficient through which to remove the therapy delivery element 190, thereby placing the retention clip 100 in an open configuration 100B, as shown in FIG. 8B. In other examples, the physician or other user can manually separate the first and second ends 102A, 104A of the retention clip 100 (for instance, using a finger) and then remove the portion of the therapy delivery element 190 out of the interior 110 of the retention clip 100 and through the separated first and second ends 102A, 104A, In this way, the retention clip 100 of the retention apparatus 200 inhibits the therapy delivery element 190 from coming out of the retention apparatus 200 at an undesired time but allows relatively easy removal of the therapy delivery element 190 from the retention apparatus 200 when it is desired (for instance, by the physician or other user) to do so.

The present inventors have recognized various advantages of the subject matter described herein. For instance, in some examples, the retention apparatus described herein can be used to retain a therapy delivery element (for instance, a stimulation lead) within packaging, thereby decreasing the chances of the therapy delivery element from inadvertently coming out of the packaging and potentially becoming damaged and/or losing sterility. While various advantages of the example retention apparatuses are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description, The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A retention apparatus comprising:

a tray including a channel configured to hold a therapy delivery element at least partially within the channel; and a retention clip that is separate and removable from the tray, wherein the retention clip is sized and shaped to fit within a portion of the channel, the retention clip configured to releasably retain the therapy delivery element within the retention clip, wherein the portion of the channel includes a recess, and wherein a shape of the retention clip is sized to fit within the recess, wherein the portion of the channel includes a lip configured to inhibit removal of the retention clip from the tray, and wherein an upper surface of the lip is coplanar with a rest of an upper surface of the tray.

2. The retention apparatus of claim 1, wherein:

the retention clip includes a first end and a second end; and with the retention clip disposed within the portion of the channel, the first end is disposed proximate the second end such that the retention clip forms a substantially closed loop to releasably retain the therapy delivery element.

3. The retention apparatus of claim 2, wherein, with the retention clip disposed within the portion of the channel, the first end and the second end overlap.

4. The retention apparatus of claim 2, wherein the retention clip includes a substantially triangular shape with a first side of the retention clip including the first end and a second side of the retention clip including the second end.

5. The retention apparatus of claim 4, wherein the first side and the second side of the retention clip are each attached to a third side of the retention clip.

6. The retention apparatus of claim 5, wherein a first hinge is disposed between the first side and the third side.

7. The retention apparatus of claim 6, wherein the first hinge includes a living hinge.

8. The retention apparatus of claim 6, wherein a second hinge is disposed between the second side and the third side.

9. The retention apparatus of claim 8, wherein at least one of the first hinge and the second hinge includes a living hinge.

10. The retention apparatus of claim 1, wherein the retention clip includes a silicone material.

11. The retention apparatus of claim 1, wherein the tray includes a polyethylene terephthalate glycol-modified (PETG) material.

12. The retention apparatus of claim 1, wherein the retention clip is configured to stick to the tray.

13. The retention apparatus of claim 6, wherein the first hinge is in direct contact with the lip.

14. A retention clip comprising:

a first side that includes a first end and a second side that includes a second end, the first end being biased proximate the second end such that the retention clip forms a substantially closed loop; and a hinge, wherein the hinge is thinner than the first side and the second side, and wherein the retention clip is configured to releasably retain a therapy delivery element within the retention clip, and wherein the retention clip is separate and removable from a tray that is configured to hold the therapy delivery element.

15. The retention clip of claim 14, wherein the retention clip is sized and shaped to fit within a complementary portion of a channel of a tray.

16. The retention clip of claim 14, wherein the first end and the second end overlap.

17. The retention clip of claim 14, wherein the retention clip includes a substantially triangular shape.

18. The retention clip of claim 17, wherein the first side and the second side of the retention clip are each attached to a third side of the retention clip.

19. The retention clip of claim 18, wherein the hinge is disposed between at least one of:

the first side and the third side; and the second side and the third side.

20. A retention apparatus comprising:

a tray including a channel configured to hold a therapy delivery element at least partially with in the channel, wherein a portion of the channel includes a recess; and a retention clip having a profile that is complementary to a profile of the recess such that the retention clip is configured to fit snugly within the recess, the retention clip being separate and removable from the tray, the retention clip configured to releasably retain the therapy delivery element within the retention clip.

* * * * *